United States Patent [19]

Grossman et al.

[11] Patent Number: 5,089,306
[45] Date of Patent: Feb. 18, 1992

[54] GLAZING DENTAL CONSTRUCTS

[75] Inventors: David G. Grossman, Corning; Michael A. Karnas, Big Flats, both of N.Y.

[73] Assignee: Corning Incorporated, Corning, N.Y.

[21] Appl. No.: 646,247

[22] Filed: Jan. 28, 1991

Related U.S. Application Data

[62] Division of Ser. No. 550,286, Jul. 9, 1990, Pat. No. 4,964,416.

[51] Int. Cl.$^5$ .................... B65D 65/14; A61C 13/08
[52] U.S. Cl. .................... 428/35.1; 428/349; 433/202.1; 433/203.1; 433/212.1; 433/226; 433/217.1
[58] Field of Search .............. 433/202.1, 203.1, 212.1, 433/217.1, 226; 428/34.1, 34.9, 35.1

[56] References Cited

U.S. PATENT DOCUMENTS 4,121,011 10/1978 Glover et al. .................... 423/347

Primary Examiner—James J. Seidleck
Assistant Examiner—Charles R. Nold
Attorney, Agent, or Firm—Milton M. Peterson; Clinton S. Janes, Jr.

[57] ABSTRACT

A glazing device, and a method for using such device to apply a surface glaze to a dental construct, are disclosed. The device comprises glazing material associated with a shrinkable, hollow carrier. The method comprises associating glazing material with a hollow carrier composed of a shrinkable and removable material, assembling the construct and carrier with the construct positioned within the carrier, shrinking the carrier onto the construct, removing the carrier, and maturing the material to a glaze. The device and method find particular application in applying coloration, either uniformly or in a pattern, to a dental construct.

11 Claims, 1 Drawing Sheet

GLAZING DENTAL CONSTRUCTS

This is a division of application Ser. No. 07/550,286, filed July 9, 1990, now U.S. Pat. No. 4,964,416.

RELATED APPLICATION

This application is related to patent application S.N., entitled GLAZING DENTAL CONSTRUCTS, filed of even date herewith in the names of D. G. Grossman, R. E. Johnson and M. A. Karnas, and assigned to the same assignee as this application.

FIELD OF THE INVENTION

The field of the invention is dental restorations, more particularly, applying surface glazing to such articles.

BACKGROUND

Preformed dental constructs may be produced in various forms, including crowns, veneers, inlays, onlays and false teeth. They may be constructed from a variety of materials, such as, ceramics, glass-ceramics, glass, porcelain, porcelain-fused-to metal (PFM), and organic materials.

Glass-ceramics found useful in producing dental constructs are described, for example, in U.S. Pat. Nos. 3,732,087 (Grossman) and 4,431,420 (Adair). These patents disclose tetrasilicic fluormica glass-ceramics having properties particularly suited to producing such articles.

As described in the patents, a molten glass is cast in a mold by a process known as investment casting. The resulting glass construct is then thermally converted to a glass-ceramic. Normally, the construct is translucent and uncolored, but colorants may be included in the glass compositions, if desired.

Recently, a new system for the manufacture of crowns and other dental constructs has been proposed. This alternative to prior casting methods involves utilizing CAD/CAM techniques to provide computer-controlled milling of a solid block to a prescribed contour. Typical systems are described, for example, in European Patent Application 0/311/214/A1 (van der Zel) and U.S. Pat. No. 4,575,805 (Moermann et al.).

The present invention is particularly convenient to use with constructs prepared by this technique, but is not so limited. Rather, it is applicable to dental constructs by whatever manner produced and from whatever material employed.

While uncolored dental constructs are technically satisfactory, appearance frequently demands coloration for cosmetic effect. It is, of course, possible to include colorants in an original glass melt, as suggested in the Grossman and Adair patents. This provides a uniform coloration which may be acceptable for such purposes as small fillings or inlays.

For larger restorations, such as veneers, crowns and onlays, a more sophisticated system of coloration is desired. For example, color gradation from the neck of a crown to the incisal edge would be desirable. Also, special effects whereby the restoration would blend with the surrounding dentition could be very useful.

This desire for variable color effects has led to a search for a surface coloration technique. One such procedure is disclosed in U.S. Pat. No. 4,650,418 (Blair et al.). In this process, multiple layers of colored porcelain glazes are successively fired onto the outside surface of a restoration. In this way, distribution of color across the surface, as well as in depth, can be varied.

The process is effective, but requires a degree of artistic talent to arrange colors for a natural effect. Thus, a technician may use a brush to place or flow a wet porcelain glaze mixture where needed. It would, obviously, be desirable to provide a simpler procedure that requires less skill in application.

PURPOSES

A basic purpose is to provide an improved procedure for applying a surface glaze to a dental construct having a complex surface.

Another purpose is to provide a surface glazing procedure that is capable of producing special color effects.

A further purpose is to provide such a surface coloration procedure that involves a colorant application step that is predictable and reproducible.

A still further purpose is to provide such a surface coloration procedure that is readily adapted to automated processing.

Another purpose is to provide a preformed glazing device adapted to application of surface glazing to a dental construct.

Another purpose is to provide such a glazing device that may be adapted to produce special color effects.

SUMMARY OF THE INVENTION

In furtherance of these and other apparent purposes, our invention contemplates a method of glazing a dental construct having a complex surface which comprises associating glazing material with a carrier in the form of a hollow, open-ended enclosure, the carrier being composed of a shrinkable and removable organic material, assembling the construct and carrier so that the construct is positioned within the carrier, subjecting the assembly to a treatment to shrink the carrier into intimate contact with the construct surface, removing the organic carrier to leave the pattern of glazing material on the construct surface, and maturing the glazing material to a glaze on the construct surface.

In one embodiment, vitreous glaze particles are admixed with one or more pigments which may be uniformly dispersed, or arranged in a desired pattern. In other embodiments, the construct is formed either by investment casting or by milling, from a glass-ceramic such as a tetrasilicic fluormica glass-ceramic, the carrier is a thermally shrinkable and removable organic that may be either a volatile or oxidizable material, the pigment and glaze particles are either dispersed in the body of the carrier or applied to the interior wall of the carrier, and the coloration varies in shade across the article surface.

A further embodiment of the invention is a preformed glazing device for applying a glaze to dental constructs that comprises glazing material, with or without admixed pigment, and a shrinkable carrier for such material.

PRIOR ART

In addition to the patents previously noted, the texts of which are incorporated herein by reference, the following United States Patents are cited of possible interest:

U.S. Pat. No. 2,391,106 (Saffir) discloses a method of forming an artificial tooth by forming a plastic resin sheath having the shape of a tooth, packing the sheath with a heat hardenable tooth material, and firing the assembly, to harden the tooth material and destroy the sheath. There is no suggestion of either shrinking or surface coloration. Also, the tooth is molded in the plastic sheath, rather than the sheath being molded on a preformed tooth.

U.S. Pat. No. 3,760,502 (Hirsch) discloses precolored, planar, veneer structures capable of being fastened to a crown for a tooth. Coacting fastening means are applied to the back of the veneer and to the front of the crown. There is no suggestion of conforming the veneer to the crown by shrinking.

U.S. Pat. Nos. 3,986,261 (Faunce) and 4,226,593 (Cohen et al.) disclose directly applying a facing or veneer, which may be precolored, to a tooth. The tooth is etched, and a preformed, flexible veneer bonded to the etched surface of the tooth. There is no suggestion in these patents of either a shrinking or a surface coloring procedure.

U.S. Pat. No. 4,512,743 (Santucci et al.) discloses applying a pigmented, polymerizable composition to an etched tooth surface to form a veneer. Like Faunce and Cohen et al., this represents a form of directly applying a veneer to a tooth. It has no relation to shrinking, or to forming of a dental construct as an independent body.

U.S. Pat. No. 4,822,279 (Greggs) discloses applying a custom-made porcelain veneer to a tooth. The veneer is stained and glazed by conventional techniques, thus providing no suggestion of the present procedure.

DESCRIPTION OF THE INVENTION

The present invention is a unique method of providing a glaze finish on a dental construct by applying glazing material over the surface of the construct and maturing the material. In one form, clear, or uncolored, vitreous glaze particles are applied, and the particles fused into a glaze finish. In another form, one or more pigments are admixed in or with the glaze particles. This provides a glaze finish with any desired coloration pattern.

It is also possible, of course, to employ inks composed of curable organic materials which are sufficiently durable after radiant curing, such as, mild thermal, or visible light, or ultraviolet to function as the coloration. This option is considered to be encompassed within the concept of glazing, and is particularly useful if the construct is also formed from an organic material.

The invention is described with respect to the use of vitreous glaze particles with pigment added, a particularly useful form in which the invention was developed. It will be understood that the same steps would be followed in producing a clear glaze, the difference being omission of the pigment materials.

Figure 1:
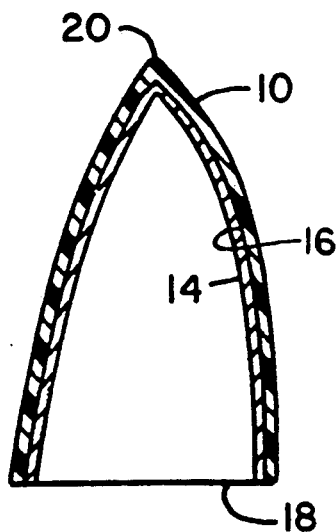
FIG. 1 is a cross-sectional view of a glazing device in accordance with the invention.

FIG. 1 of the drawing shows a hollow, open-ended enclosure 10, in the nature of a cap, adapted to use in carrying out the invention. Cap 10 will be formed from a shrinkable, organic material. Thermally-shrinkable, organic materials are well known and generally preferred. However, materials shrinkable by other forms of radiation are also known, and their use is also contemplated. Cap 10 may have the general configuration of a dental construct in conjunction with which it will be used.

Figure 2:
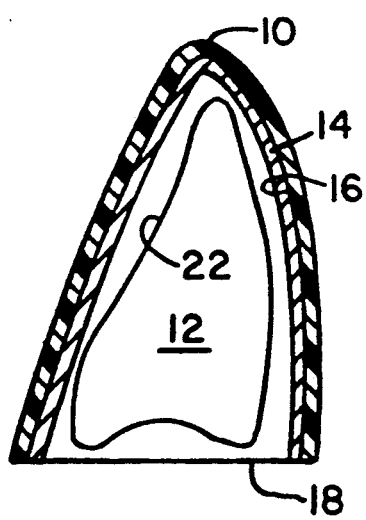
FIGS. 2 and 3 are, respectively, side and rear views, in cross-section, of a dental construct and glazing device assembly in accordance with the invention.

FIG. 2 shows cap 10 assembled with a typical construct 12 preparatory to carrying out the coloration procedure. Construct 12 is shown as an unshaded crown adapted to placement on a patient's tooth. Crown 12 may be shaped in a conventional manner, or may be milled from a glass-ceramic or porcelain block by a CAD-CAM procedure, such as referred to earlier.

As shown in FIG. 1, cap 10 has a pigmented layer 14 applied over its inner surface 16. This layer is composed of a mixture of a glaze and one or more pigments in particulate form. The glaze may be any conventional vitreous material adapted to being fired on the surface of construct 12. It will be appreciated that, if a clear glaze is desired, the pigment will be omitted.

Pigmented layer 14 may be patterned in any desired manner. Thus, the amount of pigment, and hence the ultimate color intensity, may be graduated from the open neck end 18 to the tip 20 of the cap. Alternatively, where a mixed pigment is used, the mixture ratio may be varied.

A variety of other effects may also be achieved. Thus, intense underglaze stains may be placed in the grooves along the occlusal surface of the crown 12 prior to application of cap 10. Special effects, such as white check lines, or decalcification spots, may be placed on the cap prior to application.

Another approach to variable coloration is to employ a set of two or more caps with different color effects on the applied layers 12. By trimming portions from different caps, custom build-ups may be achieved on a construct 12.

Figure 3:
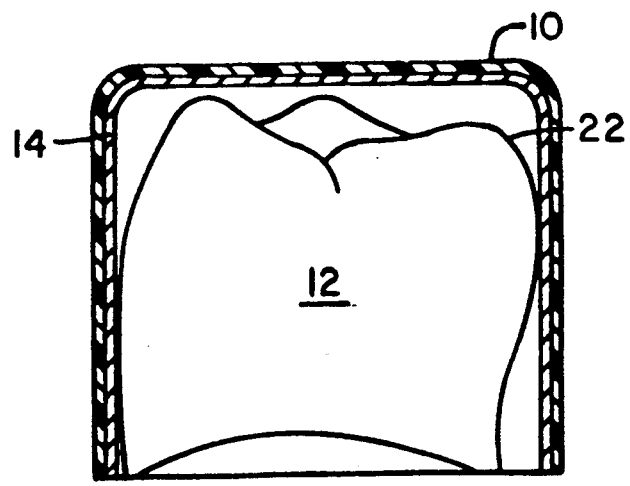

Once cap 10 is suitably patterned on its interior surface, it is placed over restoration 12 as shown in FIG. 2. FIG. 2 is an anterior view, and FIG. 3 a posterior view, of construct 12 positioned within, and enveloped by, cap 10.

The assembly is then introduced into a furnace where it is subjected to a heat schedule. This thermal treatment shrinks cap 10 into tight conformity with surface 22 of crown 12. The patterned color layer 14 is thus brought into intimate contact with surface 22.

In the course of the heat treatment, it is essential that the organic material of cap 10 be dissipated. Further, color layer 14 must remain firmly adherent to the surface of construct 12 in the pattern originally formed on or in cap 10. The maximum temperature in the heat treating schedule then must be sufficiently high so that the glaze particles in layer 14 soften and form an adherent coating on surface 22.

In addition to being shrinkable then, the material from which cap 10 is formed must be readily separable from the color pattern. Thus, cap 10 may be composed of an organic that burns off (oxidizes) during the heat treatment. Alternatively, it may be a volatile material that vaporizes. It also may be a material that is at least partially physically removable. The essential condition is that cap 10 be dissipated without disturbing the original pattern of layer 12.

Where additional color is desired, or if special effects are desired, it is possible to apply additional layers by repeating the process. For example, a restoration may be deemed too light in color after one application. In that case, an additional layer may be applied by simply repeating the entire procedure. Alternatively, the second application may be another color thus providing a blend.

Figure 4:
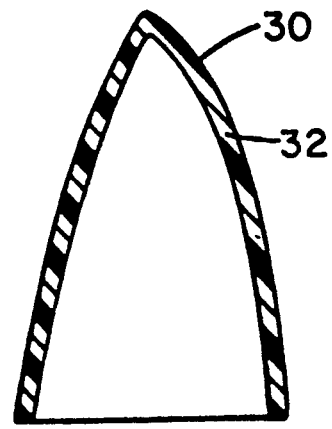
FIG. 4 is a cross-sectional view illustrating a modified glazing device.

FIG. 4 illustrates an alternative cap construction 30. In this embodiment, the glaze particles 32, with or without pigment added, are incorporated within the body of shrinkable plastic cap 30. In this event, the plastic material of cap 30 must be removed by oxidation or volatilization.

By way of specific example, an uncolored crown was formed from a tetrasilicic fluormica glass-ceramic composition as disclosed in the Adair and Grossman patents mentioned earlier.

A cylindrical length of heat-shrinkable tubing was cut to a size slightly larger than the crown. The tubing was 0.5 inch diameter SHRINK-LOC tubing available from Sinclaire & Rush, Inc. DICOR shading porcelain powder was mixed with a medium to form a suspension. A continuous layer of the suspension was applied over the entire inner surface of the tubing length.

The coated tubing was dried and placed over the crown on a setter plate. Care was taken to have the ends of the tubing extend beyond, or overlap, the crown. The assembly was placed in an oven at 600° C. The tube was observed to contract and conform to the external shape of the crown. This forced the interior coating into intimate contact with the irregular surface of the crown. The oven was heated to 850° C., the plastic tube volatilizing in the meantime. The layer of porcelain shading remained on the crown surface and matured to a glossy glaze. Upon cooling, the crown was observed to have a continuous glaze of the shading powder fused to its surface.

We claim:

1. A preformed, dental construct glazing device that comprises a dental construct glazing material carried within the body of, or on the inside wall of, a hollow, organic, shrinkable carrier having an open end and a closed end.

2. A preformed device in accordance with claim 4 wherein the glazing material is in the form of vitreous glaze particles.

3. A preformed device in accordance with claim 2 wherein the glaze particles are applied on the inside wall of the carrier.

4. A preformed device in accordance with claim 2 wherein the glaze particles are within the body of the carrier.

5. A preformed device in accordance with claim 2 wherein the glaze particles are admixed with one or more pigments to form a coloration pattern.

6. A preformed device in accordance with claim 5 wherein the coloration pattern is applied on the inside wall of the carrier.

7. A preformed device in accordance with claim 5 wherein the coloration pattern is within the body of the carrier.

8. A preformed device in accordance with claim 5 wherein the coloration pattern varies in color intensity.

9. A preformed device in accordance with claim 8 wherein the amount of pigment in the coloration pattern varies from the closed end of the carrier to the open end.

10. A preformed device in accordance with claim 1 wherein the glazing material is in the form of curable organic materials.

11. A preformed device in accordance with claim 1 wherein the carrier is thermally shrinkable.

* * * * *